US006498152B1

(12) United States Patent
Wainwright et al.

(10) Patent No.: US 6,498,152 B1
(45) Date of Patent: Dec. 24, 2002

(54) USE OF A FARNESYL TRANSFERASE INHIBITOR IN THE MANUFACTURE OF A MEDICAMENT FOR LOCAL ADMINISTRATION TO THE VASCULAR WALL IN THE PREVENTION OF RESTENOSIS

(75) Inventors: Cherry Lindsey Wainwright, Glasgow (GB); Roger Martin Wadsworth, Glasgow (GB); Nigel John Pyne, Glasgow (GB); Susan Pyne, Glasgow (GB); Lorraine Margaret Work, Glasgow (GB)

(73) Assignee: University of Strathclyde, Glasgow (GB)

( * ) Notice: Subject to any disclaimer, the term of this patent is extended or adjusted under 35 U.S.C. 154(b) by 0 days.

(21) Appl. No.: 09/674,584

(22) PCT Filed: May 11, 1999

(86) PCT No.: PCT/GB99/01266

§ 371 (c)(1), (2), (4) Date: Dec. 21, 2000

(87) PCT Pub. No.: WO99/58132

PCT Pub. Date: Nov. 18, 1999

(30) Foreign Application Priority Data

May 11, 1998 (GB) .............................................. 9809889

(51) Int. Cl.[7] .............................................. A61K 31/66
(52) U.S. Cl. ....................................................... 514/119
(58) Field of Search ......................................... 514/119

(56) References Cited

U.S. PATENT DOCUMENTS 5,510,510 A    4/1996   Patel et al.

FOREIGN PATENT DOCUMENTS

| WO | WO 96/34851 A1 | 11/1996 |
| WO | WO 97/04788 A2 | 2/1997 |
| WO | WO 97/17070 A1 | 5/1997 |
| WO | WO 97/48789 A1 | 11/1998 |
| WO | WO 99/10523 | 3/1999 |

OTHER PUBLICATIONS

International Search Report, PCT/GB99/01266, completed Sep. 16, 1999.

Manne, et al., *Ras Farnesylation as a Target for Novel Antitumor Agents: Potent and Selective Farnesyl Diphosphate Analog Inhibitors of Farnesyltransferase;* Drug Development Research, 1995, pp. 121–137, vol. 34.

Hung, et al., *The farnesyltransferase inhibitor; FPT inhibitor III upregulates Bax and Bcl–xs expression and induces apoptosis in human ovarian cancer cells,* International Journal of Oncology, 1998, pp. 137–140, vol. 12.

Hung, et al., *Involvement of caspase family proteases in FPT inhibitor III–induced apoptosis in human ovarian cancer cells,* International Journal of Oncology, 1998, pp. 1339–1342, vol. 12.

Chakrabarti, et al., *Protein prenyl transferase activities of Plasmodium falciparum,* Molecular and Biochemical Parasitology, 1998, pp. 175–184, vol. 94.

Yokoyama, et al., *The effects of protein farnesyltransferase inhibitors on trypanosomatids; inhibition of protein farnesylation and cell growth,* Molecular and Biochemical Parasitology, 1998, pp. 87–97, vol. 94.

Hightower, et al., *H–Ras Peptide and Protein Substrates Bind Protein Farnesyltransferase as an Ionized Thiolate,* Biochemistry, 1998, pp. 15555–15562, vol. 37.

*Primary Examiner*—Raymond Henley, III
(74) *Attorney, Agent, or Firm*—Alston & Bird LLP

(57) ABSTRACT

The present invention relates to the prevention of restenosis of vascular passages following surgical removal of obstructions, by means of local administration of farnesyl transferase inhibitors to the vascular wall. This allows effective use of particularly low dosages with minimal side effects.

25 Claims, 5 Drawing Sheets

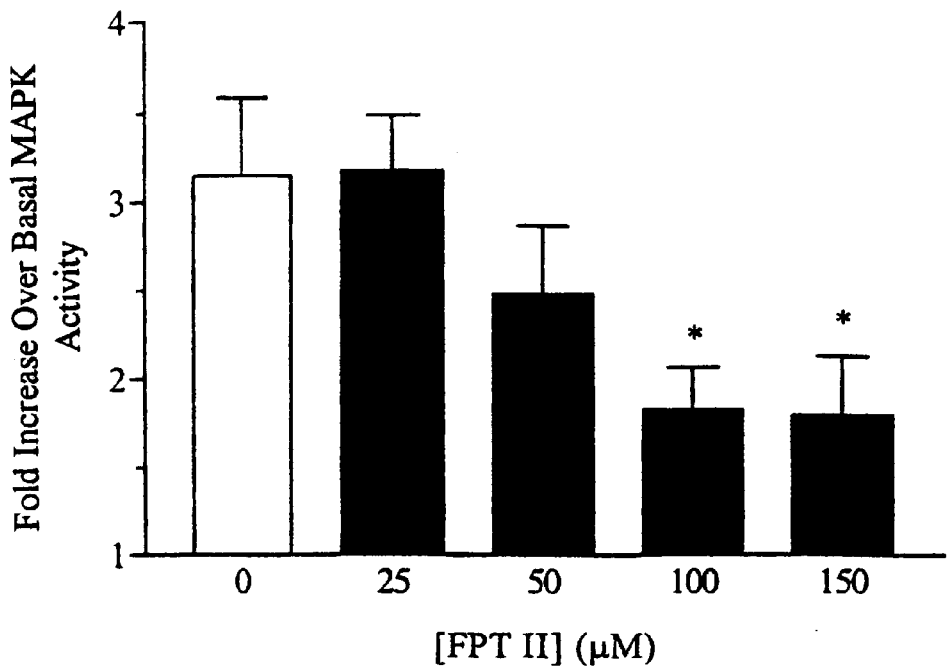
Figure 3.A(i)
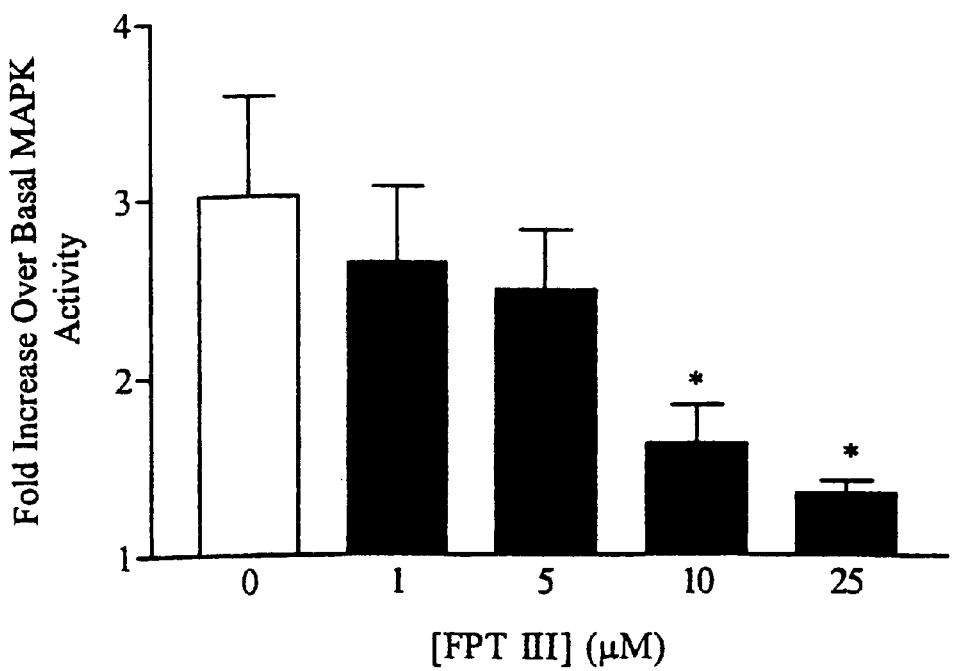
Figure 3.A(ii)

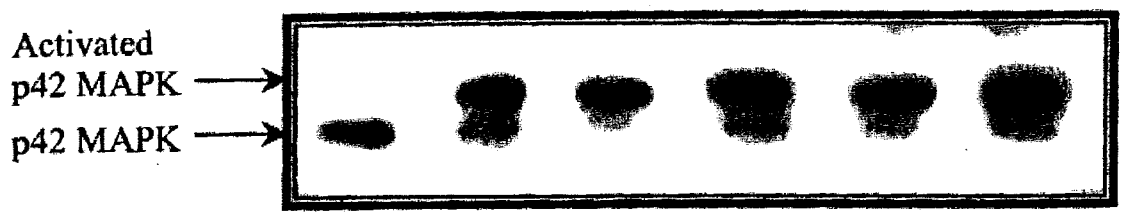
PMA (1μM)    -    +    +    +    +    +
FPT III (μM)    -    -    1    5    10    25
Figure 3.B(i)
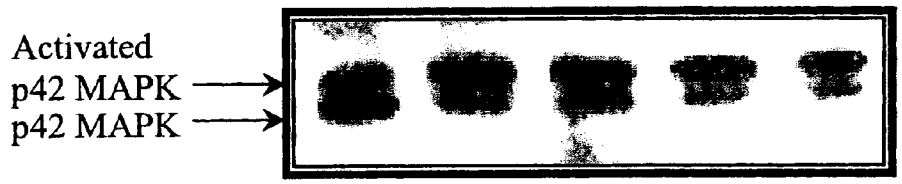
PMA (1μM)    -    +    +    +    +
FPT II (μM)    -    -    25    50    100
Figure 3.B(ii)

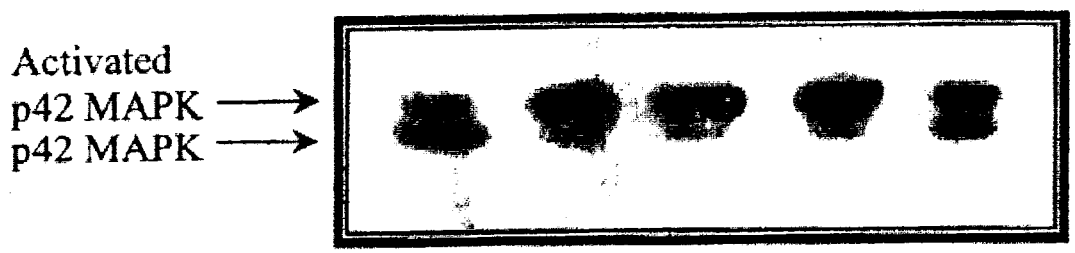
Figure 3.C
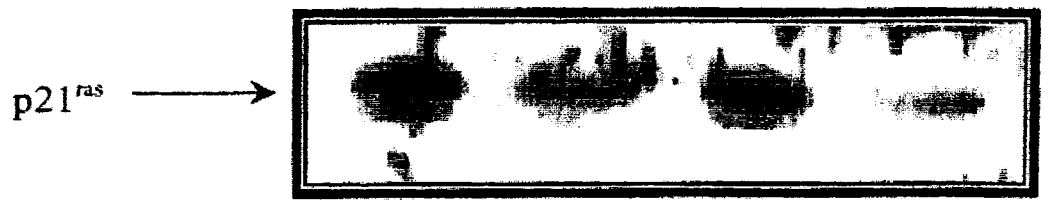
Figure 3.D

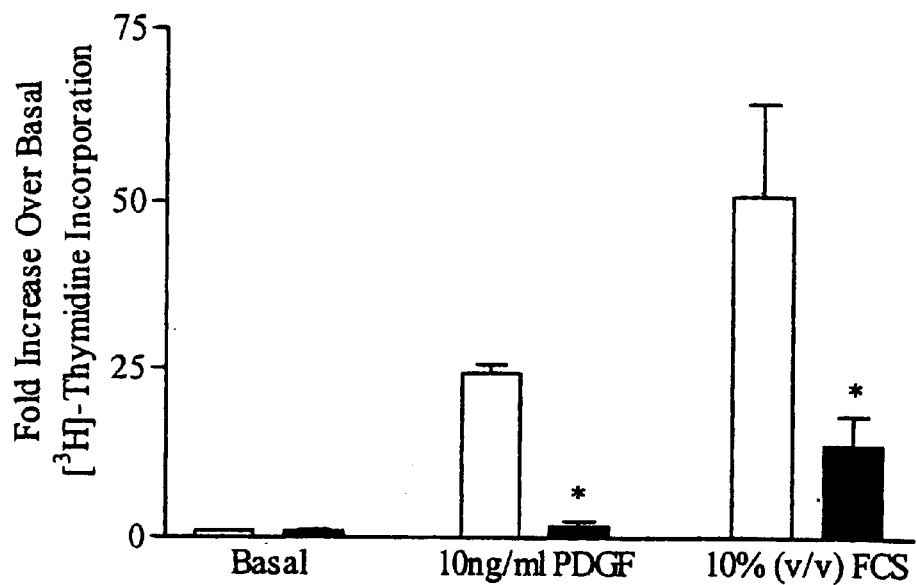
Figure 3.E(i)
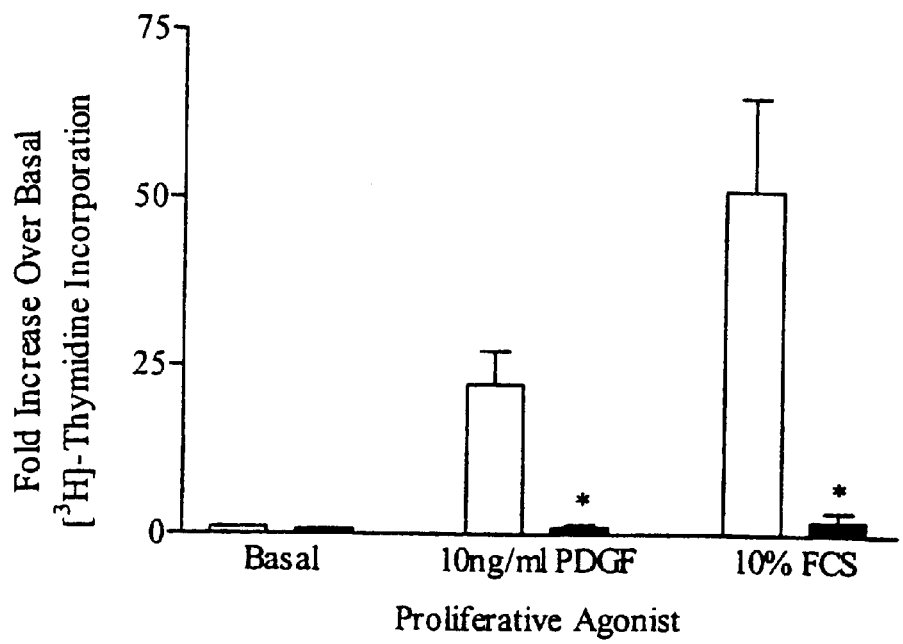
Figure 3.E(ii)

USE OF A FARNESYL TRANSFERASE INHIBITOR IN THE MANUFACTURE OF A MEDICAMENT FOR LOCAL ADMINISTRATION TO THE VASCULAR WALL IN THE PREVENTION OF RESTENOSIS

This is a 371 of PCT/GB99/01266 filed May 11, 1999,
The present invention relates to the treatment and prevention of vascular proliferative disorders such as restenosis following coronary angioplasty.

A major cause of cardiovascular disease is blockage of an artery as a result of atherosclerosis. This is especially serious in the coronary artery, but also affects arteries in other parts of the body including the head and limbs. Balloon angioplasty is a highly effective treatment for restoring blood flow through an atherosclerotic artery. It involves feeding a balloon to the affected artery and then inflating it to create an enlarged channel. However there is a relatively high rate of relapse following balloon angioplasty: 30–50% of patients experience a re-growth of tissue within the angioplastied artery that can re-occlude the lumen (a vascular proliferative condition known as restenosis), necessitating further surgery. Restenosis is due to the growth of smooth muscle-like cells within the lumen to form an abnormal lining (the neointima) that occludes the lumen of the artery.

The cell signalling molecule ras is a key molecule in the regulation of cell proliferation through the MAP kinase pathway. Correct function of ras depends upon its location at the cell membrane, which is achieved by linking it to a farnesyl moiety, that inserts specifically in the membrane. This farnesylation step is carried out by the enzyme farnesyl transferase, and thus inhibitors of farnesyl transferase will prevent ras function.

It has previously been proposed in WO97/00252 that certain tricyclic inhibitors of farnesyl transferase enzyme (FTIs) can be used in the treatment of a wide variety of proliferative diseases such as cancer, psoriasis, and restenosis. The treatments disclosed simply comprise conventional treatment regimens using oral or parenteral administration of various formulations such as tablets, capsules, liquids, pastes, gels etc and including sustained release formulations. Such treatments of proliferative diseases are normally used over extended periods of weeks or months. Given the fundamental importance of cell growth and maintenance to good health, it is not at all surprising that such treatments are normally associated with serious side effects which have an important effect on restricting the use thereof.

It is an object of the present invention to avoid or minimize one or more of the above disadvantages.

It has now very surprisingly and unexpectedly been found that a single brief local application of a farnesyl transferase inhibitor, for example, a farnesyl analogue, to the vascular wall substantially contemporaneously with a surgical procedure for removing a vascular occlusion, can substantially prevent restenosis of the vascular passage without the need for further subsequent treatments.

Without in any way wishing to restrict the scope of the present invention it is believed that the use of the farnesyl transferase inhibitors in this way inhibits the proliferation of vascular smooth muscle cells due to blocking of the MAP kinase pathway by preventing membrane incorporation of ras.

Thus in one aspect the present invention provides a farnesyl transferase inhibitor for use in the preparation of a medicament for local application to the vascular wall so as to substantially prevent restenosis of the vascular passage.

In another aspect the present invention provides a method of prophylaxis of restenosis comprising administration of an effective dosage of a farnesyl transferase inhibitor to the vascular wall substantially contemporaneously with a surgical procedure for removing a vascular occlusion, for example angioplasty.

It is a particular advantage of the present invention that restenosis can be substantially prevented, at least for extended periods of time of several weeks or months, if not indefinitely, following a single treatment, which is moreover localised to the affected area. Thus the risk of any possible side effects is substantially avoided or at least very substantially reduced when compared with conventional treatments of proliferative diseases.

Suitable farnesyl transferase inhibitors known in the art include the known Farnesyl Transferase Inhibitors FPTII and FPTIII which are commercially available from Calbiochem—Nova Biochem UK of Beeston, Nottingham, England (Manne V, et al (1995) "Ras farnesylation as a target for anti-tumour agents: potent and selective farnesyl diphosphate analogue inhibitors of farnesyltransferaseo", Drug Development Research 34, 121–137) and which have the following formulae:

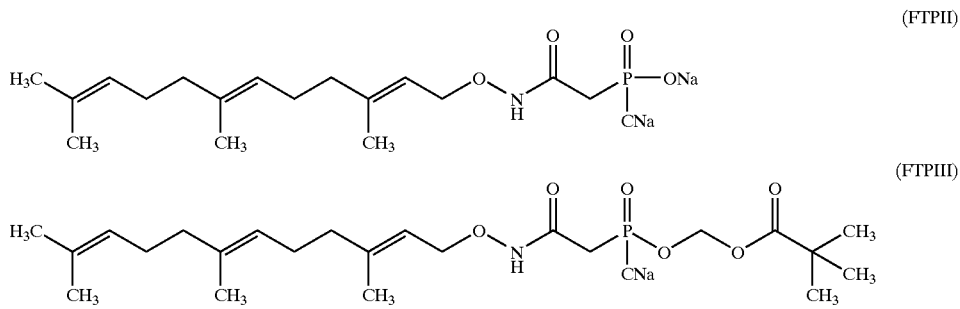

Other compounds which may be used in accordance with the present invention include arglabin which is 1,10-Epoxy-3,11(13)-guaiadien-12,6-olide including stereoisomers thereof and especially the naturally occuring stereoisomer which is believed to have the structural formula

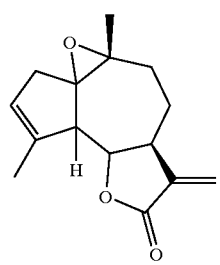

and perillol, also known as Perillyl alcohol which is 1-Hydroxymethyl-4-isopropenylcyclohexene (including both R- and S- enantiomeric forms of this compound), as well as glycosidic compounds such as those disclosed in WO97/04788, the contents of which disclosure are incorporated herein by reference to said publication. In more detail, said glycosidic compounds are compounds of formula (I):

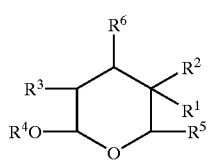

wherein $R^1$ and $R^2$ are independently selected from H, OH,

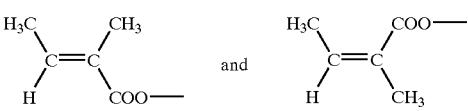

and related esters thereto;
R3 is selected from OH,

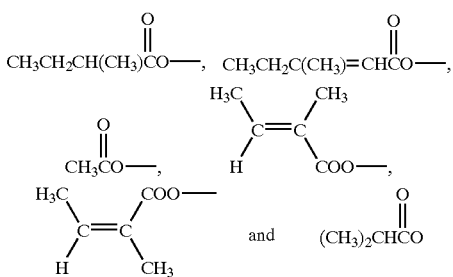

and related esters thereto;
$R^1$ is selected from $C_6$–$C_{12}$ saturated or unsaturated monocyclic or polycyclic aliphatic ring systems optionally substituted by $C_1$–$C_6$ alkyl, H, OH, =CH$_2$ or $C_1$–$C_3$ alkyl carboxyloxy or $R^1$ represents a $C_1$–$C_6$ straight- or branched-chain alkalene group substituted with such a ring system;
$R^5$ is selected from —CH$_3$, —CHO, —COOH and —CH$_2$OH and related esters and ethers derived therefrom;
$R^6$ is selected from —OH,

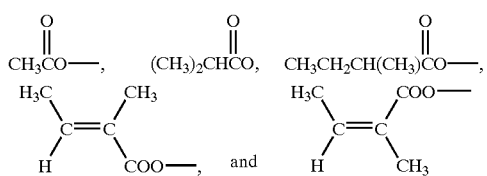

In accordance with the present invention, the farnesyl transferase inhibitors are administered substantially contemporaneously with the surgical procedures including immediately before and/or during and/or after the surgical procedure. Most conveniently administration is effected as soon as practicable after completion of the surgical procedure, typically from 1 to 60 minutes after completion of the procedure. The duration of the procedure may depend on the nature of the farnesyl transferase inhibitor used and/or of the formulation used including the concentration of the farnesyl transferase inhibitor, the nature of the vehicle, etc. Typically the farnesyl transferase inhibitor formulation is applied to the vascular wall for from 5 to 60 minutes, conveniently from 10 to 30 minutes, for example about 15 minutes.

Advantageously the area of vascular wall undergoing treatment is substantially isolated from the fluid normally flowing therethrough, during the course of application of the farnesyl transferase inhibitor formulation thereto. This may conveniently be achieved by means of a conventional dispatch catheter which defines an annular chamber between the vascular wall and the outside of a central by-pass passage through which normal vascular fluid flow can be maintained. The farnesyl transferase inhibitor formulation may thus be brought into direct contact with the vascular wall by introduction into the annular chamber without the need for interrupting the normal vascular fluid flow. This method also has the advantage of substantially restricting exposure of the patient to the formulation to only the particular area requiring treatment thereby further restricting the possibility of undesirable side effects from the treatment. In principle once the annular chamber has been filled with the liquid formulation this would simply be held therein for the required treatment period following which it may be withdrawn. In practice a small amount of leakage from the chamber into the vascular flow may be experienced so that it would normally be desirable to continue infusion of formulation at a slow rate e.g. from 10 to 1000 µl per minute, e.g. 200 µl per minute, during the treatment period to compensate for leakage losses.

In general the farnesyl transferase inhibitors are formulated with common pharmaceutical carriers and excipients into liquid formulations suitable for use in parenteral, especially intravenous, administration. Suitable liquid formulations include solutions, suspensions and emulsions, e.g. water or aqueous propylene glycol solutions. In general the formulations are substantially physiologically isotonic. The formulations may contain from $5 \times 10^{-2}\%$ to $5 \times 10^{-8}\%$ w/v of the farnesyl farnesyl transferase inhibitor, preferably from $5 \times 10^{-3}\%$ to $5 \times 10^{-7}\%$ w/v, advantageously from $5 \times 10^{-4}\%$ to $5 \times 10^{-6}\%$ w/v.

Typically there would be used a formulation with a farnesyl transferase inhibitor concentration of around 0.5 mg/l ($5 \times 10^{-5}\%$ W/V). Given a typical treatment volume of the order of 3 ml this would typically correspond to a total dosage rate of 2.5 ug per kg bodyweight of the patient. In general the farnesyl transferase inhibitors are administered at a dosage range of from 24 ng to 250 µg, preferably from 250 ng to 25 µg, per kg bodyweight. These dosage ranges may be compared with a proposed dosage rate of from 1 to 50 mg/kg bodyweight per day with the treatments disclosed in U.S. Pat. No. 5,516,807. Thus it will be apparent that the potential risk of side effects with the present invention is very dramatically reduced relative to the prior art.

Conveniently the formulations of the present invention are presented in unit dosage form, for example, in ampoules. Typically each unit dosage formulation contains from 2 µg to 12.5 mg, preferably from 20 µg to 1 mg, for example, about 125 µg, of the farnesyl transferase inhibitor. Conveniently each unit dosage contains from 1 to 10 ml, preferably from 2 to 5 ml, of liquid formulation.

Further preferred features and advantages of the invention will appear from the following examples given by way of illustration of the present invention, and with reference to the accompanying drawings wherein:

BRIEF DESCRIPTION OF THE DRAWINGS

FIGS. 3A(i) to 3E(ii) are graphs of the results of various in vitro tests on the effects of FPTII and FPTIII.

Figure 1:
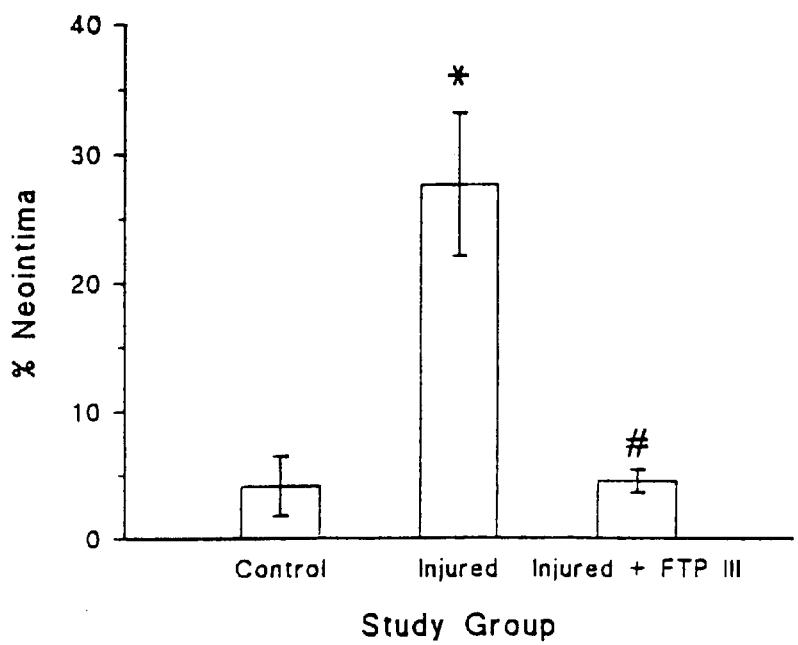
FIGS. 1 and 2 are graphs of the results of in vivo tests on the effects of FPTIII treatment in angioplasty.

EXAMPLE 1
Infusion Composition for Vascular Wall application FPT III (3.97 mg) was dissolved in sterile physiological saline (100 mls 0.9% w/v Nacl) to provide a 25 $\mu$M infusion solution.

EXAMPLE 2
Infusion Composition for Vascular Wall application FPT II (1.24 mg) was dissolved in sterile physiological saline (100 mls 0.9% w/v Nacl) to provide a 25 $\mu$M infusion solution.

EXAMPLE 3
Treatment of Pigs undergoing coronary angioplasty

A1 In vivo Coronary Angioplasty Procedure Male Large White/Welsh Landrace pigs (n=14; 14–19.5 kg) were pre-medicated with aspirin (325 mg p.o.; Bayer) 24 hours prior to surgery and continued daily for the duration of the study. All animals (n=14) were subjected to balloon angioplasty of the left anterior descending (LAD) coronary artery, with 7 pigs receiving local FPT III treatment. In each case the left circumflex (LCx) coronary artery served as a non-injured control vessel. Animals were sedated (Stresnil®, Janssen; 5 mg kg$^{-1}$ i.m), intubated and ventilated at a rate of 14 strokes min$^{-1}$. Anaesthesia was induced and maintained with a mixture of $O_2$:halothane:nitrous oxide. Antiarrhythmic cover was administered by a slow i.v. infusion of saline containing 2.03 mmol l$^{-1}$ $MgSO_4$ and 50 mg ml$^{-1}$ bretylium tosylate (Wellcome). The left femoral artery was isolated and a 7F introducer sheath (Bard UK Ltd) inserted using the Seldinger technique. A 6F guiding catheter was advanced under fluoroscopic control to the coronary ostium. An angiogram was performed and a 3 mm balloon catheter with a 0.014" steerable guidewire in the lumen advanced into position between the 1$^{st}$ and 2$^{nd}$ diagonal branch of the LAD coronary artery. The balloon was inflated 3 times to 10 atmospheres for 30 seconds with 60 second intervals between inflations.

A.2 Follow-up Procedure

Four weeks after coronary balloon angioplasty the animals were re-sedated (Stresnil®; 5 mg kg$^{-1}$ i.m.) and euthanised by an i.v. injection of sodium pentobarbitone (Euthatal®; 70 mg kg$^{-1}$). The chest was opened and the heart removed and transported to the laboratory in Krebs solution [118.4 mM-NaCl; 25 mM-$NaHCO_3$; 11 mM-glucose; 4.7 mM-KCl; 1.2 mM-$KH_2PO_4$; 1.2 mM-$MgSO_4$; 2.5 mM $CaCl_2$]. Both the LAD and LCx coronary arteries were dissected free and cut into 4 artery rings 3–4 mm in length, 2 of which were used for functional studies and the remainder fixed in formal saline for subsequent histological analysis.

B. Intra-arterial drug administration

Immediately after successful balloon angioplasty a 3 mm Dispatch™ catheter (SCIMED®) with a double lumen was advanced to the site of balloon angioplasty. Following inflation of the delivery coil to 6 atmospheres, FPT III (25 $\mu$M) was delivered over a 15 minute infusion period at a rate of 200 $\mu$l min$^-$. The catheters were removed and the femoral artery ligated distally and proximally to the incision. The wound was sutured subcutaneously and the skin closed with non-irritant silk sutures (Ethicon). Antibiotic and analgesic cover was administered on recovery from anaesthesia and subsequently as required.

Materials

Glasgow University Veterinary School provided aspirin (Bayer); Stresnil® (Janssen); halothane (Mallinkrodt Veterinary); heparin (Leo Laboratories); ligatures and sutures (Ethicon) and Amphipen LA (Mycofarm UK Ltd). Bretylium tosylate (Wellcome); $MgSO_4$ and sterile saline were supplied by the Pharmacy at Glasgow Royal Infirmary. The 6F guide catheters, 3 mm balloon catheters and 0.014 steerable guidewires (all by Advanced Cardiovascular Systems Inc, Temecula, Calif. USA) were recycled following prior use in a human patient. All catheters were sterilised prior to use and where possible, further re-used to minimise cost. The 7F catheters were purchased from Bard UK Ltd. The contrast medium hexabrix was supplied by May & Baker C. Measurement of effects of treatment C1 —Determination of Vessel Morphometry Two artery rings, both control (LCx) and balloon injured (LAD), from each heart were fixed immediately after dissection in phosphate buffered formal saline. The vessels were then processed and embedded in paraffin was. Sections were cut (5 $\mu$m) and stained using haematoxylin and eosin (H&E) before photographs were taken of the microscopic slides. The areas of the different vessel layers (adventitia, media, neointima) and the lumen space were quantified using planimetry. The photograph was traced onto tracing paper and the respective pieces of paper corresponding to each layer weighed and calibrated against a piece of paper known to be 1 mm$^2$.

C2. Statistical Analysis

The values shown are the mean ± s.e.m. of n animals. Morphological data was expressed as the area ($\mu$m$^2$) The extent of proliferation determined histologically was quantified as the number of positive staining cells expressed as a percentage of the total number of cells counted. In the case of the functional studies, the $EC_{50}$ for each vasoactive agent and $E_{max}$, for the contractile agents were calculated from concentration-response curves and compared using a One-way ANOVA followed by a Tukey test. Concentration-response curves were compared using a Two-way ANOVA followed by a Newman Keull's post test. In all cases, when p<0.05 the result was taken to be statistically significant.

D. Results

D1. Neointima formation in the control group

Qualitative analysis of the sections demonstrated that in 6 of the 7 pigs angioplastied there was neointimal proliferation evident. The neointimal lesion present appeared where the IEL (Internal Elastic Lamina) has been damaged as a result of the balloon angioplasty. In the majority of cases the control artery (LCx) appeared normal with no neointima although in 2 cases there was a mild degree of intimal thickening.

D2. Effect of intra-arterial administration of FPT III

Figure 2:
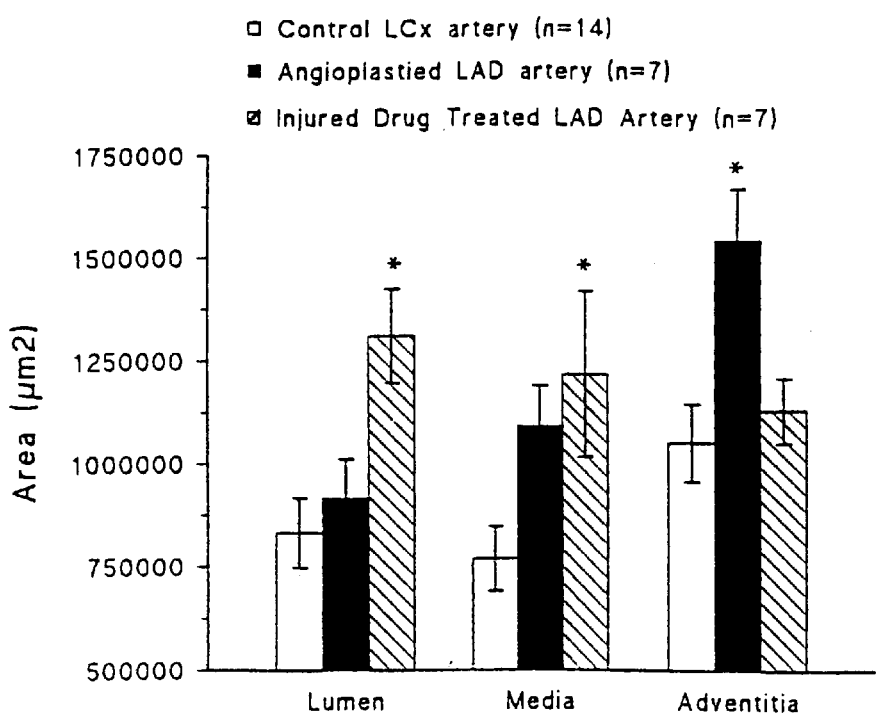

The areas of the layers in the histological sections of the arteries were quantified using planimetry. The results of the measurements are shown in FIGS. 1 and 2 in which FIG. 1 shows the effect of intra-arterial administration of FPT III on development of neointima 28 days after angioplasty. Neointina is expressed as the area of neointima as a percentage of the area within the external elastic lamina measured by planimetry of pig coronary artery n=7, * P<0.05 compared to control, # P<0.05 compared to injured. FIG. 2 shows the effect of intra-arterial administration of FPT III on the area of the lumen, media and adventitia of pig coronary artery at 28 days after angioplasty n=7, * P<0.05 compared to control.

Angioplasty in the control group resulted in the development of a substantial neointima (FIG.1), and there was also an increase in the area of the adventitial layer, with no change in the area of the vessel lumen or media (FIG. 2). In the coronary arteries treated with FPT III there was complete suppression of the development of neointima (FIG. 1). In the treated animals, the vessel lumen was enlarged (FIG. 2). However the increase in media area did not appear to be altered and the adventitial hypertrophy was reversed following drug treatment (FIG. 2).

EXAMPLE 4

In vitro activity of FPTII and FPTIII

Various in vitro studies were carried out on FPTII and FPTIII farnesyl transferase inhibitors as detailed in the FIGS. 3A to 3E below, which show a closely similar activity profile in relation to blocking of the MAP Kinase pathway, prevention of cell proliferation, and selectivity of their activity.

FIGS. 3.A (i) & 3.A (ii) show concentration-dependent inhibition of PDGF-stimulated p42/p44 MAPK activation by FPTII/FPTIII. PVSMC were pretreated with the indicated concentrations of FPTII/FPTIII (solid bars) or vehicle control (open bar) for 24 hours prior to stimulation with PDGF (10 ng ml$^{-1}$, 10 mins). P42/p44 MAPK activity was determined using the Biotrak MAPK activity assay. Values shown are means ± S.D. (n=4). *indicates p<0.05 compared to control, agonist stimulated activity using a One-way ANOVA followed by a Dunnett's test. Basal value =72.3 ±14.16 pmoles min$^{-1}$ mg$^{-1}$ cell lysate protein.

FIGS. 3.B(i) & 3.B (ii) show the lack of effect of FPTIII/FPTII on PMA-stimulated p42 MAPK activation. PVSMC were pretreated with the indicated concentration of FPTII/FPTIII or vehicle for 24 hours prior to stimulation with PMA (1 μM, 10 mins). Samples were analysed by SDS-PAGE and Western blotted using a p42 MAPK-specific antibody. Activated and inactive p42 MAPK are denoted by arrows. This is a representative result of experiments performed on 3 separate cell reparations.

FIGS. 3.C shows concentration-dependent inhibition of PDGF-stimulated p42 MAPK activation by FPTII. PVSMC were pretreated with the indicated concentration of FPTII or vehicle for 24 hours prior to stimulation with PDGF (10 ngml$^{-1}$, 10 mins). Samples were analysed by SDS-PAGE and Western blotted using a p42 MAPK-specific antibody. Activated and inactive p42 MAPK are denoted by arrows. This is a representative result of an experiment performed on 3 separate cell preparations.

FIGS. 3. D shows the effect of chronic administration of FPTII (100 μM; 24 hours) on levels of p $21^{ras}$ in the membrane fraction of PVSMC before and after PGDF (10 ng ml$^{-1}$; 10 mins) stimulation. This is a representative blot of an experiment performed on 3 separate cell preparations.

FIG. 3.E (i) shows the effect of chronic administration of FPTII (100 μM) on agonist induced DNA synthesis determined using the [$^3$H]-thymidine incorporation assay. Vehicle control (open bars) vs FPTII treated (solid bars) PVSMC. Values shown are mean±S.D. (n=4). * indicates p<0.05 compared to control agonist stimulated levels using a paired t-test. Basal value =252.06 ±96.66 cpm.

FIG. 3.E (ii) shows the effect of chronic pretreatment of PVSMC with FPTIII (25 μM) on DNA synthesis stimulated by PDGF (10 ng ml$^{-1}$) or FCS (10% v/v) determined using the [$^3$H]-thymidine incorporation assay. Vehicle control (open bars) vs FPTIII treated (solid bars) PVSMC. Values shown are mean±S.D. (n=4). * indicates P<0.05 compared to control agonist stimulated levels using a paired t-test. Basal value 247.12±93.34 cpm for FPTIII.

What is claimed is:

1. A pharmaceutical formulation for substantially preventing restenosis of a vascular passage wherein the formulation is in a form suitable for local application to the vascular wall of a vascular passage substantially contemporaneously with a surgical procedure and comprises a farnesyl transferase inhibitor in an amount of from $5\times10^{-2}$% to $5\times10^{-8}$% w/v and an excipient.

2. A pharmaceutical formulation according to claim 1, wherein the formulation is a liquid for infusion or irrigation.

3. A pharmaceutical formulation according to claim 1 or claim 7 which is in a unit dosage form.

4. A pharmaceutical formulation according to claim 3 which contains from 2 μg to 12.5 mg of the farnesyl transferase inhibitor.

5. A pharmaceutical formulation according to claim 3 which contains from 1 to 10 ml of liquid formulation.

6. A pharmaceutical formulation according to claim 1 wherein the formulation contains from $5\times10^{-3}$% to $5\times10^{-7}$% w/v of the farnesyl transferase inhibitor.

7. A pharmaceutical formulation according to claim 6 wherein the formulation contains from $5\times10^{-4}$% to $5\times10^{-6}$% w/v of the farnesyl transferase inhibitor.

8. A pharmaceutical formulation according to claim 1 wherein the excipient consists essentially of water.

9. A pharmaceutical formulation according to claim 1 wherein said excipient consists essentially of an aqueous solution of propylene glycol.

10. A pharmaceutical formulation according to claim 8 wherein the formulation is substantially physiologically isotonic.

11. A pharmaceutical formulation according to claim 1 which formulation is a slow release formulation.

12. A pharmaceutical formulation according to claim 1 wherein said farnesyl transferase inhibitor is selected from the farnesyl transferase inhibitors FPTII and FPTIII.

13. A stent for introduction into a vascular passage comprising a releasable pharmaceutical formulation which formulation is a slow release formulation for substantially preventing restenosis of a vascular passage, the pharmaceutical formulation comprising a farnesyl transferase inhibitor and an excipient.

14. A stent according to claim 13 for use in a vascular passage substantially contemporaneously with a surgical procedure and wherein said pharmaceutical formulation comprises said farnesyl transferase inhibitor in an amount of from $5\times10^{-2}$% to $5\times10^{-8}$% w/v.

15. A stent according to claim 13 wherein said pharmaceutical formulation is provided in a surface coating on the stent.

16. A stent according to claim 13 wherein the stent has a permeable portion containing said pharmaceutical formulation.

17. A stent according to claim 13 wherein said farnesyl transferase inhibitor is selected from the farnesyl transferase inhibitors FPTII and FPTIII.

18. A method of prophylaxis of restenosis of a vascular passage having a vascular wall comprising local administration of an effective dosage of a farnesyl transferase inhibitor to said vascular wall substantially contemporaneously with a surgical procedure for removing a vascular occlusion in said vascular passage.

19. A method according to claim 18 wherein the surgical procedure is an angioplasty.

20. A method according to claim 18 wherein said administration is effected at least partly via a dispatch catheter.

21. A method according to any one claim 18 in which method said surgical procedure includes the step of introduction of a stent into said vascular passage.

22. A method according to claim 21 wherein said stent is loaded with a farnesyl transferase inhibitor releasable in use of said stent in said vascular passage.

23. A method according to claim 21 wherein administration is carried out from 1 to 60 minutes after insertion of the stent.

24. A method according to claim 21 wherein administration is carried out for from 5 to 60 minutes.

25. A method according to claim 18 wherein said farnesyl transferase inhibitor is selected from the farnesyl transferase inhibitors FPTII and FPTIII.

* * * * *